US010544086B2

(12) United States Patent
Ansmann et al.

(10) Patent No.: US 10,544,086 B2
(45) Date of Patent: Jan. 28, 2020

(54) DIALKYL CARBONATES OF BRANCHED ALCOHOLS AND THEIR USE

(71) Applicant: Cognis IP Management GmbH, Düsseldorf (DE)

(72) Inventors: Achim Ansmann, Erkrath (DE); Bernd Boutty, Meerbusch (DE); Markus Dierker, Duesseldorf (DE); Stefan Bruening, Düsseldorf (DE); Rolf Kawa, Monheim (DE)

(73) Assignee: Cognis IP Management GmbH, Düsseldorf (DE)

( * ) Notice: Subject to any disclaimer, the term of this patent is extended or adjusted under 35 U.S.C. 154(b) by 0 days.

(21) Appl. No.: 15/608,117

(22) Filed: May 30, 2017

(65) Prior Publication Data

US 2017/0260123 A1 Sep. 14, 2017

Related U.S. Application Data

(63) Continuation of application No. 12/518,208, filed as application No. PCT/EP2007/010351 on Nov. 29, 2007, now abandoned.

(30) Foreign Application Priority Data

Dec. 8, 2006 (EP) ..................... 06025406

(51) Int. Cl.
| | | |
|---|---|---|
| *A61K 8/37* | (2006.01) | |
| *A61K 8/33* | (2006.01) | |
| *A61K 47/08* | (2006.01) | |
| *A61Q 19/10* | (2006.01) | |
| *C07C 69/96* | (2006.01) | |
| *C07C 68/00* | (2006.01) | |

(52) U.S. Cl.
CPC ............... *C07C 69/96* (2013.01); *A61K 8/33* (2013.01); *A61K 8/37* (2013.01); *A61K 47/08* (2013.01); *A61Q 19/10* (2013.01); *C07C 68/00* (2013.01)

(58) Field of Classification Search
None
See application file for complete search history.

(56) References Cited

U.S. PATENT DOCUMENTS

| 5,387,374 A | 2/1995 | Westfechtel et al. |
| 6,280,712 B1 * | 8/2001 | Ansmann ................. A61K 8/27 |
| | | 424/400 |
| 2005/0281770 A1 | 12/2005 | Elliott et al. |
| 2010/0331565 A1 | 12/2010 | Ansmann et al. |

FOREIGN PATENT DOCUMENTS

| DE | 4119890 A1 | 12/1992 |
| DE | 4125765 A1 | 2/1993 |
| EP | 0238946 A2 | 9/1987 |
| EP | 1083247 A2 | 3/2001 |
| EP | 1398366 A1 | 3/2004 |
| EP | 1510199 A1 | 3/2005 |
| JP | H07285829 A | 10/1995 |
| JP | 2000-095662 A | 4/2000 |
| JP | 2008-133280 A | 6/2008 |
| WO | WO-92/10462 A1 | 6/1992 |
| WO | WO-97/47282 A1 | 12/1997 |
| WO | WO-97/47583 A1 | 12/1997 |
| WO | WO-2005/074864 A1 | 8/2005 |

OTHER PUBLICATIONS

"Cream." Merriam-Webster.com. Merriam-Webster, n.d. Web. Apr. 29, 2018.*
Dierker, "Oleochemical carbonates—an overview", Lipid Technology, vol. 16, No. 6, pp. 130-133 (Jun. 2004).
Klee et al., "Triggered Release by Skin pH—Novel Encapsulation Technology for the Delivery of Personal Care Actives", SOFW-Journal, Cosmetics, vol. 132, pp. 2, 4-6, 8 (May 2006).
U.S. Appl. No. 12/518,208, Final Office Action, dated Aug. 27, 2013.
U.S. Appl. No. 12/518,208, Nonfinal Office Action, dated Apr. 30, 2012.
U.S. Appl. No. 12/518,208, Nonfinal Office Action, dated Apr. 6, 2015.
U.S. Appl. No. 12/518,208, Restriction Requirement, dated Jan. 20, 2012.

* cited by examiner

*Primary Examiner* — Alicia L Otton
(74) *Attorney, Agent, or Firm* — Marshall, Gerstein & Borun LLP

(57) ABSTRACT

The disclosure relates to dialkyl carbonates of branched alcohols and their use in cosmetic and/or pharmaceutical compositions. The disclosure more particularly relates to dialkyl carbonates in which the alkyl groups are both 2-propyl-1-heptyl groups.

3 Claims, No Drawings

DIALKYL CARBONATES OF BRANCHED ALCOHOLS AND THEIR USE

FIELD OF THE INVENTION

The invention relates to dialkyl carbonates of branched alcohols and their use in cosmetic and/or pharmaceutical preparations.

PRIOR ART

The consumer has a large number of requirements in the field of cosmetic preparations for skin and hair care: Apart from the cleansing and care effects, which determine the intended use, value is placed on such different parameters as the highest possible dermatological tolerability, good re-oiling properties, elegant appearance, optimum sensorial impression and storage stability.

Preparations which are employed for cleansing and care of human skin and of hair as a rule comprise, in addition to a number of surface-active substances, above all oil substances and water. Oil substances/emollients which are employed are, for example, hydrocarbons, ester oils and plant and animal oils/fats/waxes. To meet the high requirements of the market with respect to sensorial properties and optimum dermatological tolerability, novel oil substances and emulsifier mixtures are continuously being developed and tested.

Dialkyl carbonates of linear alcohols and their use in cosmetics are known from the prior art, for example WO 97/47282 describes the use of octyl methyl carbonate in cosmetics and EP 1 510 199 describes the use of distearyl carbonate in cosmetics. Di-n-octyl carbonate is obtainable as a cosmetics raw material under the trade name Cetiol® CC (Cognis Deutschland GmbH & Co. KG).

The preparation of dialkyl carbonates is described in WO 97/47583. The symmetric dialkyl carbonates obtainable by the process described there contain e.g. 2-ethyl-1-hexyl methyl carbonate or 2-butyl-1-octyl methyl carbonate as by-products. A use of these compounds in cosmetics is not mentioned. EP 1 083 247 describes various short-chain branched dialkyl carbonates and their suitability for washing metal surfaces.

The object of the present invention was to provide novel raw materials for cosmetic applications which have an improved profile with respect to their sensorial properties (lightness, "non-greasy feeling on the skin", softness, spreadability, absorption, ease of distribution, oiliness) and can be incorporated into a large number of cosmetic formulations, for example as an oil substance/emollient or as an agent for imparting consistency. It should be possible for the raw materials to be incorporated both into W/O and into O/W formulations, and in particular they should be compatible with crystalline UV filters, pigments, antiperspirants, salts and silicones. It was of particular interest to provide raw materials which have a good or improved dissolving power for pigments or inorganic UV filters.

It has been found, surprisingly, that the dialkyl carbonates of the present invention achieve this object and in particular lead to sensorially light products. Surprisingly, the dialkyl carbonates of the present invention are suitable in particular for dissolving polar compounds, in particular pigments or inorganic UV filters. An easier formulation of these active compounds in cosmetic and/or pharmaceutical preparations is thus achieved.

DESCRIPTION OF THE INVENTION

Dialkyl carbonates are esters of carbonic acid of the general formula $O=C(OR)_2$, wherein R denotes an alkyl radical. Dialkyl carbonates are named either by preceding the term "carbonate" by the alkyl substituents, or as carbonic acid "alkyl" esters. Thus e.g. $O=C(OC_8H_{17})_2$ is called dioctyl carbonate or carbonic acid dioctyl ester, or e.g. $O=C(OC_2H_5)(OC_8H_{17})$ is called ethyl octyl carbonates or carbonic acid ethyl octyl ester. In the following, the formula R—O—CO—O—R is used for the dialkyl carbonates.

The invention provides dialkyl carbonates of the formula (I)

$$R^1O\text{—}CO\text{—}OR^2 \qquad (I),$$

wherein
 $R^1$ is a 2-propyl-1-heptyl radical and $R^2$ represents linear or branched or cyclic hydrocarbon radicals having 1 to 22 carbon atoms and 0 or 1 to 3 double bonds, or
 $R^1$ is a 2-ethyl-1-butyl radical, $R^2$ represents linear or branched or cyclic hydrocarbon radicals having 1 to 22 carbon atoms and 0 or 1 to 3 double bonds, wherein $R^2$ is not 2-ethyl-1-butyl.

In a preferred embodiment of the invention, $R^1$ differs from $R^2$. In a preferred embodiment of the invention, $R^1$ and $R^2$ are a 2-propyl-1-heptyl radical. This embodiment of the invention thus relates to di-(2-propyl-1-heptyl) carbonate.

The invention also provides dialkyl carbonates the formula (II)

$$R^3O\text{—}CO\text{—}OR^4 \qquad (II)$$

wherein $R^3$ is chosen from the group consisting of the isodecyl radical, neodecyl radical, isoundecyl radical, isododecyl radical, isotridecyl radical, 2-pentylnonyl radical, 2-hexyldecyl radical, 2-heptyl-undecyl radical, isostearyl radical, 2-octyl-dodecyl radical, 2-butyl-1-octyl radical and 2-ethyl-1-hexyl radical, and $R^4$ represents linear or branched or cyclic hydrocarbon radicals having 1 to 22 carbon atoms and 0 or 1 to 3 double bonds, wherein $R^3$ is not identical to $R^4$, excluding 2-butyl-1-octyl methyl carbonate and 2-ethyl-1-hexyl methyl carbonate.

The invention also provides dialkyl carbonates of the formula (II)

$$R^3O\text{—}CO\text{—}OR^4 \qquad (II)$$

wherein $R^3$ is chosen from the group consisting of the isodecyl radical, neodecyl radical, isoundecyl radical, isododecyl radical, isotridecyl radical, 2-pentylnonyl radical, 2-hexyldecyl radical, 2-heptyl-undecyl radical, isostearyl radical and 2-octyl-dodecyl radical and $R^4$ represents linear or branched or cyclic hydrocarbon radicals having 1 to 22 carbon atoms and 0 or 1 to 3 double bonds, wherein $R^3$ is not identical to $R^4$.

2-Hexyldecyl methyl carbonate is particularly preferred in the context of the invention.

The invention also provides dialkyl carbonates of the formula (III)

$$R^5O\text{—}CO\text{—}OR^6 \qquad (III),$$

in which $R^5$ represents linear or branched or cyclic hydrocarbon radicals having 1 to 22 carbon atoms and 0 or 1 to 3 double bonds and $R^6$ represents branched hydrocarbon radicals having more than 12 carbon atoms and 0 or 1 to 3 double bonds.

A preferred embodiment of the invention relates to dialkyl carbonates of the formula (III)

$$R^5O\text{—}CO\text{—}OR^6 \qquad (III),$$

in which $R^5$ represents linear or branched or cyclic hydrocarbon radicals having 1 to 22 carbon atoms and 0 or 1 to 3 double bonds and $R^6$ represents branched hydrocarbon radicals having more than 12 carbon atoms and 0 or 1 double bond, wherein $R^5$ is not identical to $R^6$.

The invention also provides dialkyl carbonates of the formula (V)

$$R^9O—CO—OR^{10} \quad (V),$$

in which $R^9$ represents branched or cyclic hydrocarbon radicals having 1 to 22 carbon atoms and 0 or 1 to 3 double bonds and $R^{10}$ represents branched hydrocarbon radicals having more than 12 carbon atoms and 0 or 1 to 3 double bonds, excluding methyl-(2R,6R,3E)-6,10-dimethyl-3,9-undecadien-2-yl carbonate.

The invention also provides the use of the dialkyl carbonates of the formulae (I),(II), (III) and (V) in cosmetic and/or pharmaceutical preparations.

The invention also provides the use of dialkyl carbonates of the formula (IV)

$$R^7O—CO—OR^8 \quad (IV)$$

in which $R^7$ represents branched hydrocarbon radicals having 3 to 22 carbon atoms and 0 or 1 to 3 double bonds and $R^8$ represents linear or branched or cyclic hydrocarbon radicals having 1 to 22 carbon atoms and 0 or 1 to 3 double bonds and wherein $R^7$ is not identical to $R^8$, in cosmetic and/or pharmaceutical preparations.

In a preferred embodiment of the invention, dialkyl carbonates of the formula (IV) are used, excluding

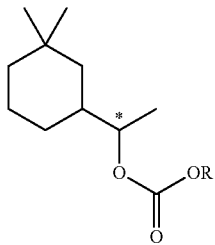

wherein R represents methyl, ethyl or isopropyl.

In a preferred embodiment of the invention, dialkyl carbonates of the formula (IV) in which $R^8$ represents branched or linear hydrocarbon radicals having 3 to 22 carbon atoms and 0 or 1 to 3 double bonds are used.

In a preferred embodiment of the invention, dialkyl carbonates of the formula (IV) in which $R^8$ represents branched hydrocarbon radicals having 3 to 22 carbon atoms and 0 or 1 to 3 double bonds are used.

In a particularly preferred embodiment of the invention, dialkyl carbonates of the formula (IV) which contain a total carbon number of greater than 12 are used.

$R^2$, $R^5$ and $R^8$ can be linear or branched or cyclic hydrocarbon radicals having 1 to 22 carbon atoms and 0 or 1 to 3 double bonds, $R^4$ can be linear or branched or cyclic hydrocarbon radicals having 2 to 22 carbon atoms and 0 or 1 to 3 double bonds. $R^7$ can be branched hydrocarbon radicals having 3 to 22 carbon atoms and 0 or 1 to 3 double bonds.

$R^6$ can be branched hydrocarbon radicals having more than 12 carbon atoms and 0 or 1 double bond. $R^{10}$ can be branched hydrocarbon radicals having more than 12 carbon atoms and 0 or 1 to 3 double bonds. $R^9$ can be branched or cyclic hydrocarbon radicals having 1 to 22 carbon atoms and 0 or 1 to 3 double bonds.

Linear alkyl radicals which may be mentioned as examples are: methyl, ethyl, butyl, pentyl, hexyl, heptyl, octyl, nonyl, decyl, undecyl, undecenyl, dodecyl, tridecyl, tetradecyl, pentadecyl, hexadecyl, heptadecyl, octadecyl, octadecenyl, nonadecyl, eicosanyl (=C20), docosanyl (=C22) radicals.

Branched alkyl radical which may be mentioned as examples are: 2-methylpropyl, iso-butyl, iso-pentyl, such as e.g. 2,2,-dimethylpropyl (=neopentyl), 3-methylbutyl (=isopentyl), iso-hexyl, i-octyl, such as e.g. 2-ethyl-hexyl or 3-ethyl-hexyl or 4-ethylhexyl or 5-ethylhexyl radicals, i-decyl radicals, such as e.g. the trimethylheptyl radical (=neodecyl radical), isostearyl, isooctyl, isononyl, isodecyl, isotridecyl, 2-ethylbutyl, 2-ethylhexyl, 2-propylheptyl, 2-butyloctyl, 2-butyldecyl, 2-hexyloctyl, 2-hexyldecyl, 2-hexyldodecyl, 2-octyldecyl radical.

Cyclic alkyl radicals which may be mentioned are the borneyl and isoborneyl radical and cyclohexyl radical.

The invention also provides the use of all the abovementioned dialkyl carbonates in cosmetic preparations. It has been found, surprisingly, that the dialkyl carbonates according to the invention are particularly suitable for the preparation of cosmetic preparations, and they are suitable in particular as oil substances/emollients and/or agents which impart consistency in cosmetic preparations. The dialkyl carbonates according to the invention are furthermore suitable for the preparation of pharmaceutical preparations, wherein the dialkyl carbonates are employed as technical auxiliary substance, such as e.g. oil substances. The dialkyl carbonates according to the invention can serve for the preparation of cosmetic preparations, such as, for example, hair shampoos, hair lotions, foam baths, shower baths, creams, gels, lotions, alcoholic and aqueous/alcoholic solutions, emulsions, wax/fat compositions, stick preparations, powders or ointments. These compositions can furthermore contain as further auxiliary substances and additives mild surfactants, oil substances, emulsifiers, pearlescent waxes, agents which impart consistency, thickening agents, overgreasing agents, stabilizers, polymers, silicone compounds, fats, waxes, lecithins, phospholipids, biogenic active compounds, UV light protection factors, antioxidants, deodorants, antiperspirants, antidandruff agents, film-forming agents, swelling agents, insect repellents, self-tanning agents, tyrosine inhibitors (depigmentation agents), hydrotropic substances, solubilizers, preservatives, perfume oils, dyestuffs and the like. The use of the dialkyl carbonates as oil substances is preferred.

The dialkyl carbonates according to the invention can be used in cosmetic formulations as so-called "light emollients" in order to establish specific properties, such as e.g. spreading properties or volatility. The dialkyl carbonates according to the invention furthermore make it possible to prepare cosmetic formulations of stable viscosity.

Preparation

The preparation of the dialkyl carbonates is carried out by processes known to the person skilled in the art, for example by transesterification of lower dialkyl carbonates, such as, for example, dimethyl carbonate, diethyl carbonate, dipropyl carbonate or dibutyl carbonate, with the corresponding alcohols or alcohol mixtures in the presence of a catalyst, as described, for example, in WO 97/47583.

Other preparation processes are described in M. Dierker: Lipid Technology, 2004, 16(6), p. 130-134.

EXAMPLES

Example 1

Preparation of Hexyldecyl Methyl Carbonate 1,350 g (15 mol) of dimethyl carbonate were initially introduced into a 4 l stirred apparatus with a dropping funnel with 14 g of sodium methylate (30% strength in methanol) and the mixture was heated up to 80° C. 699 g (1.5 mol) of hexyldecanol were then added dropwise over a period of 2 hours and the mixture was subsequently stirred at 80° C. for a further 9 hours. During this period, the methanol formed was distilled off from the reaction mixture over a distillation attachment. GC evaluation of the crude product gave a composition of: 4% of hexyldecanol, 79% of asymmetric hexyldecyl methyl carbonate and 13% of symmetric di-hexyldecyl carbonate.

The pH was adjusted to pH 3-4 with 14 g of $H_3PO_4$ (85% strength) and excess dimethyl carbonate was distilled off. The sodium phosphate which had precipitated out was filtered off with suction and the product was fractionated. The reaction product, hexyldecyl methyl carbonate, is obtained as a colorless oil with a boiling point of 125-125° C. under 0.4 mbar.

Example 2

Formulations with Hexyldecyl Methyl Carbonate

The following cosmetic recipes were prepared with the hexyldecyl methyl carbonate prepared according to Example 1. All the data are in wt. %.

| Recipe no.<br>Trade name (INCI name) | 1 | 2 |
|---|---|---|
| Dehymuls ®LE (PEG-30 dipolyhydroxystearate) | 5.00 | 4.00 |
| Lameform ®TGI (polyglyceryl-3 diisostearate) | 0.00 | 2.00 |
| Hexyldecyl methyl carbonate | 20.00 | 20.00 |
| $MgSO_4 \cdot 7H_2O$ | 1.00 | 1.00 |
| Glycerol 99.5% | 5.00 | 5.00 |
| Formalin soln. 37% strength | 0.15 | 0.15 |
| Dist. water | to 100 | to 100 |

| Recipe no.:<br>Trade name (INCI name) | 3 | 4 | 5 |
|---|---|---|---|
| Emulgade ® PL 68/50 (cetearyl glucoside (and) cetearyl alcohol) | 4.50 | 0.00 | 0.00 |
| Eumulgin ® VL75 (lauryl glucoside (and) polyglyceryl-2 dipolyhydroxystearate (and) glycerol) | 0.00 | 4.50 | 0.00 |
| Eumulgin ® B2 (ceteareth-20) | 0.00 | 0.00 | 2.00 |
| Hexyldecyl methyl carbonate | 16.00 | 16.00 | 16.00 |
| Carbopol ® 980 (carbomer) | 0.00 | 0.30 | 0.00 |
| Lanette ® O (cetearyl alcohol) | 0.00 | 0.00 | 5.00 |
| KOH (20% strength) | 0.00 | 0.60 | 0.00 |
| Glycerol 99.5% | 3.00 | 3.00 | 3.00 |
| Formalin soln. 37% strength | 0.15 | 0.15 | 0.15 |
| Dist. water | to 100 | to 100 | to 100 |

The invention claimed is:

1. A cosmetic and/or pharmaceutical preparation comprising a dialkyl carbonate according to formula (I) in an amount effective to impart consistency in the cosmetic and/or pharmaceutical preparation, wherein:
   formula (I) is $R^1O$—CO—$OR^2$, $R^1$ is a 2-propyl-1-heptyl group, and $R^2$ is a 2-propyl-1-heptyl group; and
   the preparation is free from silicone compounds and UV light protection factors.

2. The cosmetic and/or pharmaceutical preparation of claim 1, wherein the preparation is in a form selected from the group consisting of hair shampoos, hair lotions, foam baths, shower baths, creams, gels, lotions, alcoholic solutions, aqueous/alcoholic solutions, emulsions, wax compositions, fat compositions, stick preparations, powders, and ointments.

3. The cosmetic and/or pharmaceutical preparation of claim 1, further comprising an auxiliary substance selected from the group consisting of surfactants, oil substances, emulsifiers, pearlescent waxes, consistency agents, thickening agents, over-greasing agents, stabilizers, polymers, fats, waxes, lecithins, phospholipids, biogenic active compounds, antioxidants, deodorants, antiperspirants, antidandruff agents, film-forming agents, swelling agents, insect repellants, self-tanning agents, tyrosine inhibitors, hydrotropic substances, solubilizers, preservatives, perfume oils, dyestuffs, and combinations thereof.

\* \* \* \* \*